United States Patent [19]
Maida

[11] Patent Number: 6,151,528
[45] Date of Patent: Nov. 21, 2000

[54] METHOD AND DEVICE FOR APPLICATION OF ENDERMIC ELECTROTHERAPEUTIC TREATMENTS TO A HUMAN BODY

[75] Inventor: Massimo Maurizio Maida, Marina di Massa, Italy

[73] Assignee: Innuendo S.r.l., Italy

[21] Appl. No.: 09/229,537

[22] Filed: Jan. 13, 1999

Related U.S. Application Data

[63] Continuation-in-part of application No. 08/794,140, Feb. 3, 1997, abandoned.

[30] Foreign Application Priority Data

Feb. 7, 1996 [IT] Italy .................................. MI96A0217

[51] Int. Cl.[7] ........................................ A61N 1/00
[52] U.S. Cl. ......................... 607/149; 607/152; 600/388; 600/395
[58] Field of Search ............... 607/46, 152, 50, 607/115, 139, 140, 148, 149, 72, 74–76; 600/384, 390, 396, 388, 389, 393, 395

[56] References Cited

U.S. PATENT DOCUMENTS

| | | | |
|---|---|---|---|
| 3,610,250 | 10/1971 | Sarbacher | 607/149 |
| 3,954,100 | 5/1976 | Sem-Jacobsen | 600/372 |
| 4,317,457 | 3/1982 | Guillot | 607/50 |
| 4,708,149 | 11/1987 | Axelgaard et al. | 607/152 |
| 4,723,552 | 2/1988 | Kenyon et al. | 607/46 |
| 4,729,377 | 3/1988 | Granek et al. | 128/639 |
| 5,269,304 | 12/1993 | Matthews | 607/46 |
| 5,374,283 | 12/1994 | Flick | 607/46 |
| 5,507,290 | 4/1996 | Kelly et al. | 128/644 |
| 5,766,236 | 6/1998 | Detty et al. | 607/149 |

*Primary Examiner*—Linda C. M. Dvorak
*Assistant Examiner*—David M. Ruddy
*Attorney, Agent, or Firm*—Shlesinger, Fitzsimmons & Shlesinger

[57] ABSTRACT

A method for carrying out endermic electrotherapeutic treatments by employing pulse-current generator (12) and a garment (11) adapted to be worn by a patient. The garment (11) is comprised of a plurality of electrically conductive discrete portions (13, 14, 15) for contact with relatively large areas of the patient's skin, and connected with insulating portions (16) intermediate between said conductive portions. The conductive portions (13, 14, 15) are provided with respective terminals (17, 18, 19) connected to the generator (12) by conductors (20, 21, 22).

11 Claims, 2 Drawing Sheets

METHOD AND DEVICE FOR APPLICATION OF ENDERMIC ELECTROTHERAPEUTIC TREATMENTS TO A HUMAN BODY

RELATED APPLICATION

This application is a continuation-in-part of my application Ser. No. 08/794,140, filed Feb. 3, 1997, now abandoned.

BACKGROUND OF THE INVENTION

The present invention relates to a method and device for application of electrotherapeutic treatments, in particular for treating pathologies such as cellulitis.

For curing a patient of these pathologies, several different treatments are now employed, which differ from each other based on the utilized operation principles. One of these treatments is represented by electrolipolysis. It consists in creating a localized electric field, generally by driving needle-shaped electrodes into the skin. Passage of electric current through the cellulitis mass causes a local increase in the production of substances capable of promoting removal of fats from the inside of the cells.

Another treatment consists of iontophoresis utilizing the migration principle of ions from within an electric field of weak-intensity current to cause penetration of drugs and active ingredients into the deepest layers of the skin through capillaries, sweat glands and hair follicles. The electric field is applied locally by plate electrodes, wrapped into a spongy cloth saturated with an aqueous solution of the selected drug. Iontophoresis is generally employed as an alternative solution to mesotherapy which, on the contrary, consists in executing multiple microinjections of specific medicaments into the cellulitis mass. Often associated with iontophoresis is a treatment phase providing application, by means of said electrodes, of the so-called Koltz waves, which deeply penetrate into the muscles causing the spontaneous contraction of same and therefore performing a sort of passive exercise.

Another typology of treatments against cellulitis is represented by ultrasonic hydrolipoclasis taking advantage of particular needle-shaped probes applied to the skin surface to utilize the lipolitic effect of ultrasonic waves.

It is apparent that during some of the above treatments (electrolipolysis mesotherapy, ultrasonic idrolipoclasis) microtraumas may occur due to penetration of needles into the skin, in particular in the case of sensitive skin with fragile and superficial capillaries.

In addition, in the known art, electrotherapeutic treatments must be carried out by medical staff, at qualified centres.

Since many sessions spaced in time are necessary in order to achieve good results, this brings about the inconvenience that the patient must each time go to the session place to be submitted to treatment, which results in a temporary interruption of his/her working activity. On the other hand, application of these treatments on one's own is of difficult accomplishment, due to the understandable difficulties encountered by the patient in preparing and positioning the electric-field generating circuit, in particular in the case in which the electrodes consist of needles.

It is also to note that these sessions are generally expensive, so that the long-lasting therapy involves a very high total cost for the patient.

It is a general object of the present invention to obviate the above mentioned drawbacks by providing a device enabling a patient to be submitted to the application of endermic electrotherapeutic treatments without the intervention of medical staff and without any necessity to address to qualified centres.

It is a further object of the invention to provide a device enabling elimination of microtraumas and capillary breakings due to the needle penetration into the skin.

SUMMARY OF THE INVENTION

In view of the above objects, in accordance with the present invention, a method and device for carrying out endermic electrotherapeutic treatments has been devised which comprises a pulse-current generator and a garment to be worn by a patient, in which the garment is comprised of a plurality of electrically conductive discrete portions for contact with the patient's skin and connected to insulating portions intermediate between said conductive portions, the conductive portions being provided with respective terminals connected to the current generator by conductors.

It is apparent that a device in accordance with the invention, since it can be personally worn by the patient, enables treatments to be constant in time, offering improved results as compared with a series of individual application sessions, at a lower total cost. In addition, since cellulitis is a pathology that is likely to recur easily in time, the device of the invention can be reutilized on the occasion of subsequent therapeutic application cycles which the patient will be eager to execute, since all inconveniences and commitments connected with a treatment in a specialized centre are eliminated.

It is to be noted that the electrically conductive elements to be utilized for the conductive portion of the sheath garment being the object of the invention can be variously selected from those known per se. For example, fabrics in which the fibre is twisted with at least one conductive wire are known and they are used to make garments such as wollen underwear, shirts, etc. in order to attenuate potential differences taking place between the different parts of the human body, thereby creating a substantial equipotentiality.

Such an electrically conductive fabric can be used to form discrete portions of the garment being part of the device in accordance with the invention, that is to accomplish discrete electric-current application areas, intentionally creating between said areas potential differences to be utilized for therapeutic purposes.

BRIEF DESCRIPTION OF THE DRAWINGS

In order to better explain the innovatory principles of the present invention and the advantages it offers over the known art, a possible embodiment applying said principles will be described hereinafter, by way of example, with the aid of the accompanying drawings, in which.

DETAILED DESCRIPTION OF THE INVENTION

Figure 1:
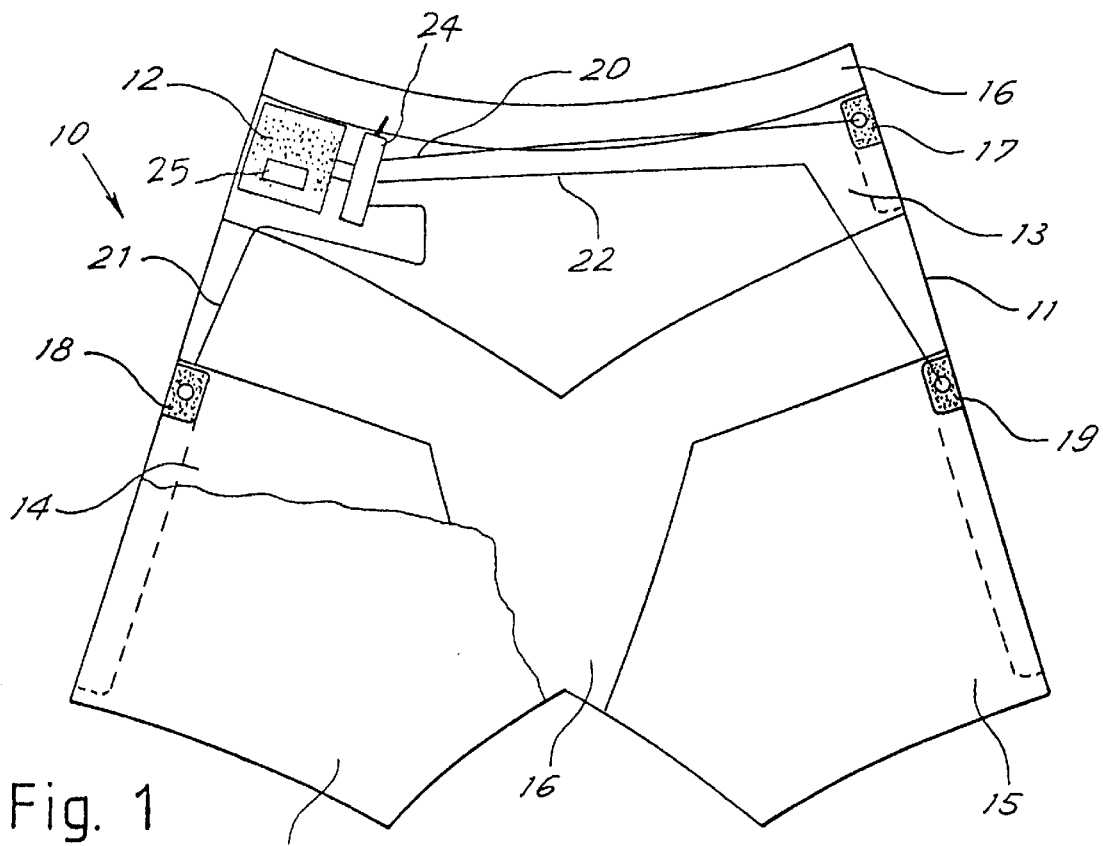
FIG. 1 is an elevation front view of the device in accordance with the invention.
Figure 2:
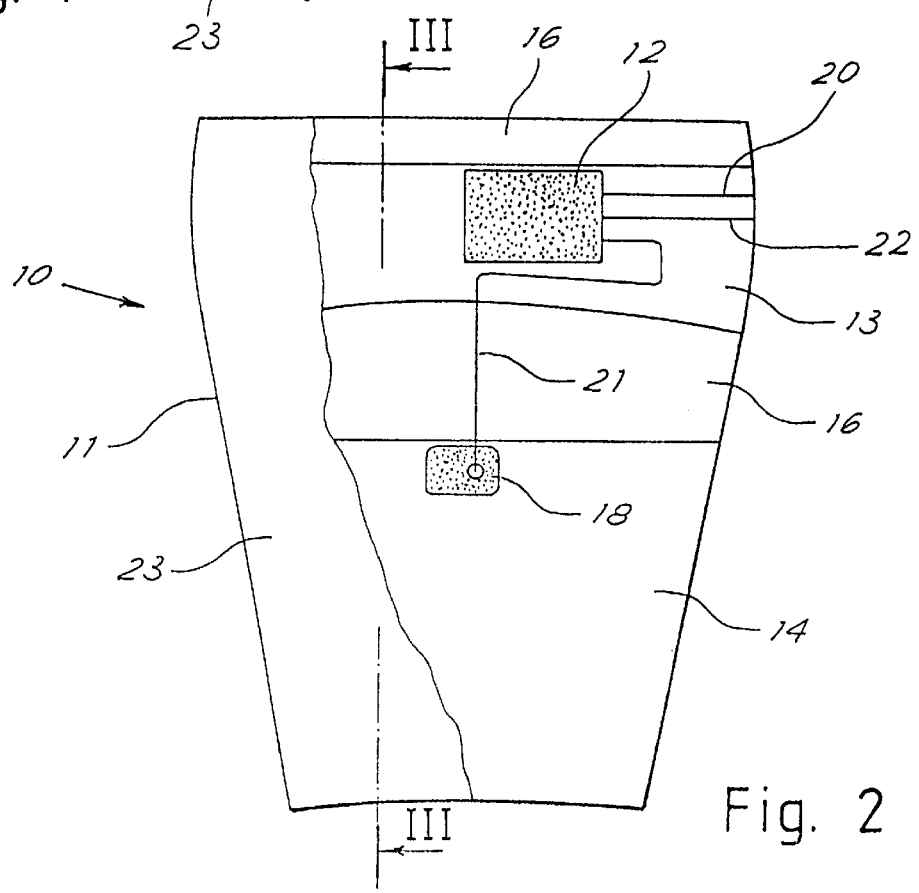
FIG. 2 is an elevation side view of the device in FIG. 1 seen from the right.

A device 10 for executing endermic electrotherapeutic treatments is shown in FIGS. 1 and 2. It comprises an element briefly identified as a garment 11, adapted to be worn by a patient, and a current generator 12. In this embodiment, the garment 11 is shown in a form adapted to cover the patient's abdomen, glutei and thighs by elastically wrapping them, for direct treatments to these parts of the human body.

Figure 3:
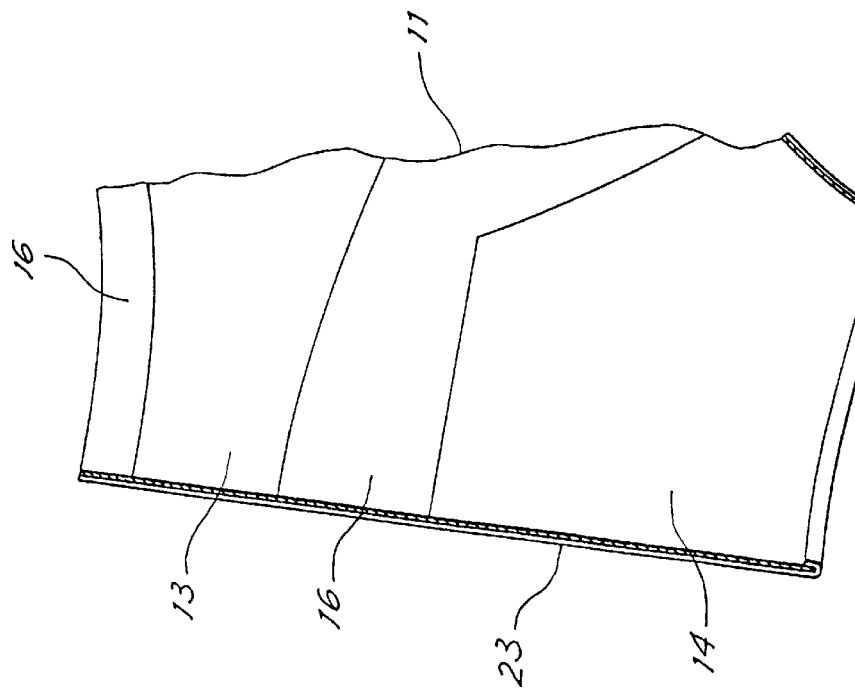
FIG. 3 is a sectional view taken along line III—III in FIG. 2.

According to the innovatory principles of the present invention, the garment or sheath 11 consists of a layer of fabric with a plurality of discrete portions thereof having electrically conductive and insulating features, respectively. With reference to the preferred embodiment of the device shown in FIGS. 1 to 3 of the drawings, electrically conductive portions of the fabric layer are denoted by 13, 14 and 15 and are disposed at the patient's waist (sheath belt) and thighs (sheath leggings) respectively, whereas insulting sheath portions are generally denoted by 16, and they separate the individual conductive portions from each other. In the example herein described three conductive portions 13, 14 and 15 are shown, each covering a rather large surface area of the patient's skin, preferably at least 80 cm.² thereby to distribute current homogeniously beneath the patient's skin. For particular requirements however, the sheath or garment 11 can be formed with a different number of conductive portions, disposed according to different configurations. At the conductive portions 13, 14, 15 there are electrical contact means or strips 17, 18, 19 respectively each provided with a sticky surface for steady application or sewn. The conductive portions are connected to generator 12 by respective clips and conductor wires 20, 21, 22. The insulating portions 16 can be made of a common non-conductive fabric, such as cotton. The conductive portions 13, 14, 15 on the contrary, are made to advantage of a cotton yarn consisting of textile fibres and metal wire. A yarn that has offered excellent results is that known under the trade name "Kind Star" (Registered Trademark), and comprises an electro-conductive cotton yarn made of textile fibers and micro-fiber of metallic alloy by the Italian firm Industrie Tessili Avianesi. The contact means 17, 18, 19 can extend along the conductive fabric (as shown in broken lines in FIG. 1) so as to ensure a good electric contact with the conductive fabric portions. It is therefore ensured also a good equipotentiality of the surface area of each portion 13, 14, 15, thus avoiding electrical breaks due to seams, breakings or ladders of the conductive fabric.

The use of a conductive fabric is advantageous also due to its structural likeness with the non-conductive fabric to which it is connected for obtaining the whole garment, so that the garment manufacture using machines of known type is facilitated. However, a material having behavioral features similar to those of a fabric, even with a different structure can be also used. A garment having the disclosed structure allows a good wearableness and does not hinder the normal sweating, and thus can be used for a long time.

A non-woven fabric or the like film having features of electrical conductivity can be utilized for the purpose, which fabric must be in any case connected to the adjacent non-conductive portions of the garment following the most appropriate technologies based on the constituent material, and therefore by sewing, gluing, welding and the like.

Obviously the conductive material, typically a metal material in any case incorporated in the garment wall, is required to have high features in terms of being inoxidizable and resisting acid corrosion, also taking into account the electrolytic effect of the carried currents and the environment where treatment is executed. The conductive and insulating portions of the fabric layer or sheath can be externally covered with an insulating coating layer 23, for example consisting of an elastic fabric of the type sold by DuPont under the trade name "Lycra" (Registered Trademark), to give the garment the required consistency and elasticity. The coating layer 23, only partly represented in FIGS. 1 and 2, can be clearly seen in FIG. 3 where, for the sake of clarity, it has been shown without the section-indicating chain line. This coating layer promotes adhesion of the conductive portions of the layer of fabric to the human body.

Generator 12 can be of reduced bulkiness (taking into account the wear currents involved), preferably of a portable type powered by an internal battery 25 or an AC/DC adapter. It can be of a known type in terms of circuits and adapted to generate electric currents characterized by waves known as "H waves", to create appropriate electric fields between the conductive portions of the sheath. Shown in FIG. 4 is a graph voltage-time of a current wave to be utilized with the device of the invention.

Figure 4:
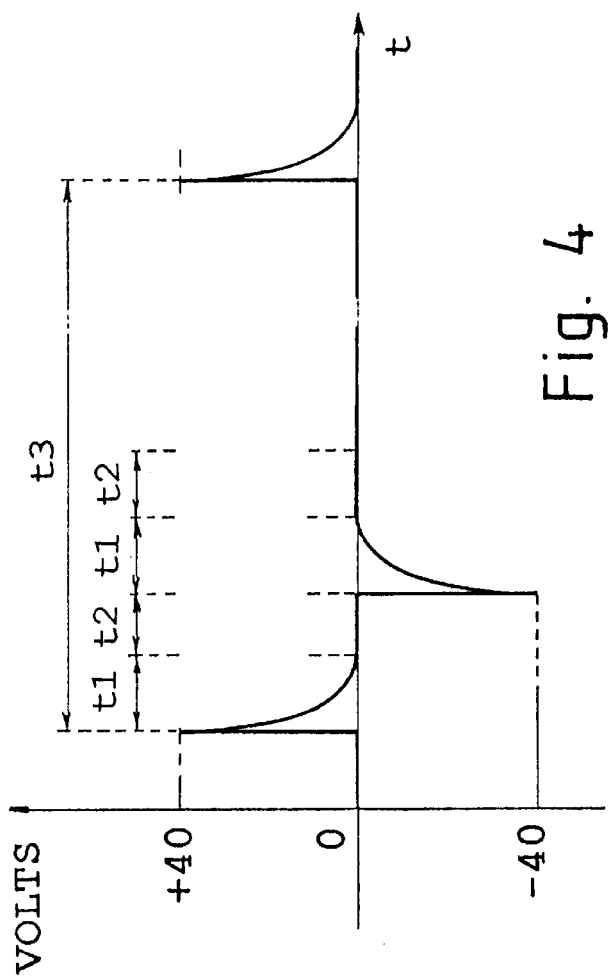
FIG. 4 is a graph showing an example of a waveform of the electric current that can be utilized by the device of the invention.

As can be viewed, the wave of current produced in each conductive portions 13–15 is formed of trains of alternating voltage pulses having a voltage output adjustable between ±20 to ±80 volts, for example adjusted to ±40 volts as shown in FIG. 4. The current output can be restricted at approximately 40 milliseconds.

With reference to the FIG. 4, experimental tests gave optimal characteristic values for times t1, t2, t3 corresponding to:

t1=1 millisecond;

t2=0.7–1 milliseconds;

t3=1000 milliseconds.

The initial edge of successive trains of voltage pulse are spaced by t3 time. Each train consists of four positive/negative pulses, one such positive/negative pulse being shown in FIG. 4 by the intervals t1, t2, t1, t2. In that case, each train of four such pulses will last 15 milliseconds (with t2=1 millisecond), and will be followed by no pulse for 985 milliseconds.

A current with such a configuration has shown its capability of activating the blood and lymphatic microcirculations in a very satisfactory manner at the areas concerned with cellulitis pathologies, and of increasing the metabolic activity of the cells, resulting in a therapeutic action on cellulitis.

Generator 12 comprises a device 24 (e.g. a switch) for selection of the connections of the generator outputs to the three electrically conductive poles 13, 14, 15. In this way, different circuit configurations can be obtained and consequently different operating modes of the sheath. For example, the generator can be connected to the two electrically conductive poles of the sheath leggings (connected parallel to each other) and the waist pole. As an alternative solution, the generator can be connected to the leggings poles, and the waist pole can be disconnected.

At this point it is apparent that the innovatory device of the invention enables achievement of the intended purposes.

Obviously, the above description of an embodiment applying the innovatory principles of the present invention is given for purposes of illustration only and is not to be interpreted as a limitation of the scope of the patent rights herein claimed.

For example, the sheath 1 shape can be different than that herein shown and can vary depending on the body area concerned with treatment. In particular, it may comprise other portions adapted to completely cover the patient's legs, thus taking the form of tights.

In addition, it is to note that the sheath 1 in accordance with the invention, by generating appropriate electric fields between predetermined descrete portions of the sheath, enables application of treatments typical of electrolipolysis for stimulating the blood circulation and the production of given body substances, without excluding the possibility of using it for iontophoresis treatments for introduction of drugs and active ingredients through the skin.

Also solved are the problems of the prior art connected with the difficulty in conveniently positioning the electrodes by unskilled persons.

An essential advantage of the invention is represented by the fact that the patient, by merely wearing the garment, is automatically able to position the electrode conductive areas in a correct manner. For the above reason, every possibility of a wrong positioning is excluded and the patient is not required to have any ability and specific preparation, which qualities are on the contrary needed for positioning of free electrodes onto the human body, as provided by the known art.

The generator can be hung to the belt so as to allow an optimal freedom of movement.

What is claimed is:

1. A device for carrying out endermic therapeutic treatment of cellulitis, comprising a pulse-current generator and a layer of fabric forming a garment adapted to be worn by a patient, said layer of fabic including a plurality of spaced electrically conductive discrete portions thereof made of a cotton yarn fabric consisting of textile fibres and metal wire, and disposed to be engaged with spaced areas of the patient's skin, and insulating portions thereof made of cotton yarn fabric and extending between and interconnecting said conductive portions, each of the conductive portions of said layer being made to engage at least an 80 cm.$^2$ surface area of the patient's skin, and being provided with respective terminals connected to the generator by conductors, thereby to distribute electric current homogeneously through the engaged portions of said skin.

2. A device according to claim 1, characterized in that each of said terminals comprises an elongate, electrical conductor strip secured to a respective conductive portion of said layer of fabric.

3. A device according to claim 2, characterized in that the discrete electrically conductive portions consist of a first conductive portion in the form of a belt disposed at the patient's waist, and second and third conductive portions in the form of leggings disposed at the patient's thighs.

4. A device according to claim 2, characterized in that the conductive portions and insulating portions are externally covered with an insulating coating layer giving the garment particular elasticity.

5. A device according to claim 1 characterized in that the current generator is adapted to generate electric currents with H waves, to create electric fields between the conductive portions of the garment, and wherein the H wave produced in each conductive portion is formed of trains or alternating pulses separated by 15 milliseconds and having maximum voltage values of +80 volts and a duration of 1 millisecond each pulse, each train having four positive/negative pulses.

6. A device according to claim 3, characterized in that the current generator comprises a device for selectively connecting the output of the generator to the electrically conductive portions so as optionally to connect the generator output only to the second and third conductive portions or to the second and third conductive portions and the first conductive portion.

7. A method for curing a patient of cellulitis by means of an endermic electrotherapeutic treatment, comprising providing a layer of fabric and forming a garment adapted to be worn by the patient, said layer of fabric including a plurality of spaced electrically conductive discrete portions thereof made from a cotton yarn consisting of textile fibers and metal wire, and insulating portions thereof made of a cotton yarn fabric and extending in said layer between and interconnecting said conductive portions, positioning each of said conductive portions in said fabric layer so as to engage at least 80 cm.$^2$ of the patient's skin when the garment is worn, providing the conductive portions of said layer with respective terminals connected to a pulse current generator by electric conductors, and causing said generator to apply a pulsating current to said conductive portions of said fabric layer, and to discrete portions of the patient's skin engaged by such conductive portions, thereby to distribute the pulsating current continuously and homogeneously just beneath the patient's skin through the cellulitic mass.

8. A method according to claim 7, including causing the pulsating current to be applied at the patient's waist and at the patient's thighs by means of respective portions of said spaced electrically conductive discrete portions.

9. A method according to claim 7, including causing the pulsating current to be applied onto the patient's skin in the form of a H-waves current, to create electric fields between said discrete, wide portions of the patient's skin.

10. A method according to claim 9, including causing the H-wave to be made of trains of alternating voltage pulses, each train having a length of 15 milliseconds and maximum voltage values of +80 volts and consisting of four positive/negative pulses, each pulse having a duration of 1 millisecond.

11. A method according to claim 10 including causing the initial edges of successive trains of voltage pulses to be spaced by 1000 milliseconds.

* * * * *